United States Patent [19]

Wang et al.

[11] Patent Number: 4,638,064

[45] Date of Patent: Jan. 20, 1987

[54] PROCESS FOR PREPARING ETHYLENICALLY UNSATURATED HETEROCYCLIC THIOCARBONYL COMPOUNDS AND THEIR ORGANO-OXYLATED PRECURSORS

[75] Inventors: Pen-Chung Wang, Midland, Mich.; James M. Renga, Walnut Creek, Calif.

[73] Assignee: The Dow Chemical Company, Midland, Mich.

[21] Appl. No.: 718,754

[22] Filed: Apr. 1, 1985

[51] Int. Cl.$^4$ .............. C07D 279/04; C07D 277/04; C07D 277/06; C07D 327/02; C07D 327/04; C07D 327/06; C07D 333/22; C07D 333/24; C07D 335/02; C07D 333/16; C07D 337/04; C07D 339/02; C07D 339/08

[52] U.S. Cl. ...................... 544/54; 548/182; 549/10; 549/11; 549/14; 549/21; 549/28; 549/30; 549/36

[58] Field of Search ............ 544/54; 548/182; 549/10, 11, 14, 21, 28, 30, 36

[56] References Cited

U.S. PATENT DOCUMENTS 4,301,258 12/1981 Lal et al. .
4,340,690 7/1982 Lal et al. .
4,459,411 7/1984 Wang .

OTHER PUBLICATIONS

*Justus Liebigs Am. Chem.*, 722, p. 132 at 137–138 (1969).
*Nouveau Journal De Chimie*, 7(5), pp. 269–270 (1983), "Thioglyoxal: Its Argon–Matrix Isolation in the Photolysis of Vinylene Thiocarbonates".
*Tetrahedron Letters*, No. 52, pp. 5007–5010 (1979).
*Beilsteins Handbuch Der Organischen Chemie*, p. 134 (1910), p. 658 (1910–1919).
*Tetrahedron Letters*, No. 21, pp. 2557–2558 (1980).
*Z. Chem.*, vol. 4, No. 10, p. 386 (1964), "The Synthesis of Glucosides of 4-Hydroxycinnolines or Cinnolone-(4) and Their Thioanalogs".
*Z. Chem.*, vol. 4, No. 10, p. 387 (1964), "Reaction of Zinc Diethyl with Alpha–Mono– and Alpha Alpha'–Dibrominated, Aliphatic Dicarboxylic Acid Esters".

*Primary Examiner*—Veronica P. Hoke

[57] ABSTRACT

Unsaturated heterocyclic carbonyl-containing compounds, such as 2-oxathiolone, are prepared by the oxylation of saturated heterocyclic carbonyl-containing precursors of the above compounds in a $C_{1-4}$ alcohol or carboxylic acid solvent in the presence of a supporting electrolyte followed by dehydroxylation of the oxylated intermediate.

The products formed may be polymerized or copolymerized with other ethylenically unsaturated monomers to prepared resins, films, etc. or they may be employed as reaction intermediates.

13 Claims, No Drawings

PROCESS FOR PREPARING ETHYLENICALLY UNSATURATED HETEROCYCLIC THIOCARBONYL COMPOUNDS AND THEIR ORGANO-OXYLATED PRECURSORS

BACKGROUND OF THE INVENTION

This invention relates to a process for preparing organo-oxylated heterocyclic thiocarbonyl compounds and their unsaturated derivatives.

Unsaturated heterocyclic thiocarbonyl compounds are useful monomers for polymerization and copolymerization processes, e.g., to prepare resins and films. The compounds are further useful as intermediates in the preparation of pharmaceuticals and other organics. For example, the reaction of 2-oxathiolone

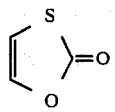

with anthracene to produce

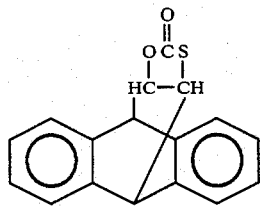

is described in *Justus Liebigs Am. Chem.*, 722, page 132 at 137–138 (1969). Also, 2-oxathiolone decomposes in an argon matrix photolysis at 10 Kelvin (K), when irradiated with electromagnetic radiation of a wavelength of 254 nanometers into the thioglyoxal represented by the formula

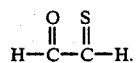

B. Gebhardt and R. Mayer in *Z. Chem.*, 4(10), 386 (1964) report the production of 2-oxathiolone by dehydrating ethylenethiocarbonate

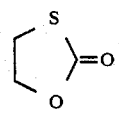

with N-bromosuccinimide. A yield of about 50 percent was obtained of a colorless liquid with a boiling point of 70° C. to 72° C. at a pressure of 12 millimeters of mercury.

It would be desirable to have a process to produce unsaturated heterocyclic thiocarbonyl compounds without consuming expensive N-bromosuccinimide.

SUMMARY OF THE INVENTION

The present invention is an oxylating process comprising contacting a heterocyclic thiocarbonyl compound with an oxylating agent under conditions sufficient to form oxylated derivative of the heterocyclic thiocarbonyl compound.

In a more limited embodiment of the invention, the process comprises the additional step of dehydroxylating the oxylated compound to produce an ethylenically unsaturated derivative of the oxylated compound.

For the purposes of this application, anodic oxylating means the process of electrochemically alkoxylating or acyloxylating a compound. The heterocyclic thiocarbonyl compound is preferably an aliphatic heterocyclic compound having a thiocarbonyl moiety

in the heterocyclic ring and is represented by the formula:

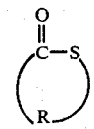

in which R is a divalent organic moiety capable of: (1) forming a heterocyclic ring including the thiocarbonyl moiety and (2) undergoing a substitution reaction with the oxylating agent. The oxylating agent is an alkoxylating agent or an acyloxylating agent. The oxylated derivative is a heterocyclic thiocarbonyl compound represented by the formula

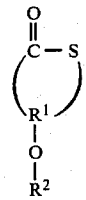

in which $R^1$ is a trivalent organic moiety similar to R except that it has been substituted with the monovalent $-OR^2$ moiety. $R^2$ is alkyl or acyl. The ethylenically unsaturated derivative is preferably a heterocyclic thiocarbonyl compound represented by the formula:

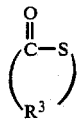

in which $R^3$ is a divalent organic moiety similar to R except it includes an ethylenically unsaturated moiety which is bonded to the sulfur atom of the heterocyclic ring.

The ethylenically unsaturated heterocyclic thiocarbonyl compounds are useful as reaction intermediates, solvents and monomers to prepare resins, films and the like.

DETAILED DESCRIPTION OF ILLUSTRATIVE EMBODIMENTS

The oxylating process of this invention comprises contacting a heterocyclic thiocarbonyl compound (precursor) with an oxylating agent, i.e., an alcohol or a carboxylic acid or their salts in an electrolysis cell in the presence of a supportive electrolyte under conditions sufficient to form an alkoxylated or acyloxylated derivative of the heterocyclic thiocarbonyl compound (oxylated compound). The heterocyclic thiocarbonyl compound used as the starting material optionally bears one or more inert substituents provided that both the ring carbon bound to the sulfur (the α carbon), and the next adjacent carbon (the β carbon), each bear a hydrogen. In more preferred embodiments, this process also comprises a dealkoxylation or deacyloxylated step whereby the alkoxylated or acyloxylated derivative is converted to an ethylenically unsaturated heterocyclic thiocarbonyl compound (unsaturated compound).

Generally, preferred embodiments of this invention comprise charging an electrolysis cell with the precursor, the oxylating agent and a supporting electrolyte. The reactants are then subjected to conditions sufficient to cause the precursor to be oxylated with the oxylating agent without significant cleaving of the heterocyclic moiety or reaction with the thiocarbonyl moiety on the precursor. Preferred is alkoxylation.

The precursor is preferably represented by the formula

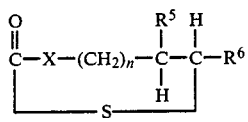

in which
X is selected from the group of bivalent moieties O, S, $CR^7R^8$ and $NR^9$ (X is more preferably either O or $NR^9$);
$R^5$, $R^6$, $R^7$, $R^8$ and $R^9$ are independently selected from the group of monovalent moieties hydrogen, lower alkyl, aryl and acyl; and
n is between 0 and about 15 (even more preferably between 0 and about 3 and most preferably 0).

Precursors are well-known and commercially available or they may be prepared by known techniques. For example, bubbling phosgene through a methylene chloride solution of the proper β mercaptan alcohol and Bronsted base at room temperature will produce the desired precursor. The β mercaptan alcohol can be purchased or produced by bubbling hydrogen sulfide through the appropriate alkene oxide. Preferred precursors are monothioethylene carbonates, 4,5-alkyl-substituted monothioethylene carbonates, p-thiobutyrolactone, ethylene dithiocarbonate, 5-phenyl-p-thiobutyrolactone, tetrahydrothiopyran-2-one and N-methyl-2-thiazolidone. The most preferred precursor is monothioethylene carbonate.

The oxylating agent is preferably aliphatic alcohol or carboxylic acid having from 1 to about 4 carbon atoms or their salts represented by the formula $R^4OM_{1/y}$, where $R^4$ is alkyl or acyl and M is either hydrogen or a metal cation of charge y. More preferred are the salts of alcohols of carboxylic acids having from 1 to about 4 carbon atoms. Most preferred is sodium acetate.

The supporting electrolyte is a conducting salt selected to provide the necessary conductivity during oxylation and to be otherwise inert towards the formation of by-products. To be effective, the reacting solution has to support a current flow between electrodes placed in the reaction solution under reaction conditions. Preferred are electrolytes which result in reacting solutions with conductivities of 0.004 Mhos or larger. More preferred are those producing conductivities of 0.04 or larger. Suitable supporting electrolytes are well-known in the art and generally include alkali metal, alkaline earth metal (such as Mg and Be), ammonium and quaternary ammonium salts of perchloric acids; Lewis acids, such as tetrafluoroborohydrate, $BF_3$, $FeCl_3$, and hexafluorophosphoric acid; Bronsted acids, such as hydrofluoric acid, nitric acid, hydrochloric acid, and sulfuric acid; lower carboxylic acids, lower alkyl sulfonic acids or $C_{6-12}$ aryl sulfonic acids; and salts of the Bronsted acids. Preferred are the listed electrolytes. Acetic acid salts are particularly effective in acetic acid solvent, whereas quaternary ammonium salts of p-toluene sulfonic acid are otherwise preferred. Mixtures of conducting salts may also be employed. The supporting electrolyte is present in an amount sufficient to support the current flow necessary for the reaction to proceed under reaction conditions. Preferred are current densities between about 0.01 amps/square centimeter ($A/cm^2$) and 1.00 $A/cm^2$. Most preferred are current densities between about 0.50 and 0.90 $A/cm^2$. Alternatively, the supporting electrolyte is present from about 1 percent to about 20 percent by weight of the total electrolysis solution.

Generally, molar ratios of precursor to oxylating agent from about 1:1 to about 1:100 are employed. Preferred is a ratio from about 1:2 to about 1:50. The components of the process may be combined in any order. Preferably, the oxylating agent is employed both as reactant and solvent. However, a solvent that allows the reaction to occur may be employed.

While the above three components have been described as present during the anodic oxylation process, additional compounds may optionally be present. Small amounts of water may be present without deleteriously affecting the course of the reaction. It may also be beneficial when employing an alkanol to provide a small amount of basic material, particularly a base that is resistant to oxidation such as 2,6-lutidine, to help protect the reactants and products against a drop in pH.

Oxylation is effected by passing an electric current through the electrolytic solution using electrodes. The cathode is generally constructed of either carbon or base metals, such as steel, nickel, copper and the like. Anodes are generally formed of inert conducting materials such as carbon (as in the form of graphite, vitrous carbon, etc.), lead dioxide or noble metals and alloys thereof, or base metals coated with a noble metal. A preferred cathodic material is steel. A preferred anodic material is carbon.

Anodic oxidation is well-known. The teaching of U.S. Pat. No. 4,459,411 is hereby incorporated by reference as teaching the well-known details of this process.

The oxylation is carried out at temperatures which allow the oxylation to occur. Preferably, the electrolyte is at temperatures at which it is a liquid solution. More preferred temperatures are from about −20° C. to about the boiling point of the electrolytic solution. Even more preferred temperatures are from about 0° C. to about 70° C. While any current flow which allows the reaction to proceed at an acceptable rate is suitable, current densities of from about 0.01 to about 1 $A/cm^2$, and cell voltages from about 4 volts to about 15 volts are preferably employed. Additional features, such as the shape of the electrodes, the presence of cell divisions such as by diaphragms to form separate anodic and cathodic chambers, and use of continuous processes may be selected according to the characteristics of the particular reaction as known in the art.

Atmospheric pressure is usually employed. Elevated or reduced pressure may also be selected, although no advantage is known to result from such a selection. Preferably, the cell is purged with an inert sweep gas to remove hydrogen gas formed at the cathode during the process to reduce any explosion hazard.

A substantially complete conversion of the precursor simplifies recovery of the oxylated compound. Complete conversion of the precursor should occur when about 2 Faradays of electrons per mole of precursor in the reacting solution has passed through the cell.

When the oxylation is substantially complete, the electrolysis is terminated, preferably in a monotonic step-wise method. Any remaining alkanol or carboxylic acid is removed by distillation leaving relatively pure oxylated compound and precipitated supporting electrolyte.

The oxylating process produces an oxylated compound which is preferably of the following formula, which is optionally substituted as is the precursor:

$$\begin{array}{c} O \\ \| \\ C-X-(CH_2)_n-\underset{|}{\overset{R^5}{C}}-\underset{|}{\overset{R^6}{C}}-OR^4 \\ \phantom{C-X-(CH_2)_n-C}H \\ \underline{\phantom{XXXXXX}S\phantom{XXXXXX}} \end{array}$$

in which X, $R^4$, $R^5$, $R^6$ and n are previously defined.

The process of removing the oxylation substituent from one carbon atom and a hydrogen from an adjacent carbon atom (dehydroxylation process) can often be carried out according to known techniques. Many of the oxylated compounds may be dehydroxylated by simple pyrolysis optionally in the presence of a catalyst. The oxylated compound is heated to a temperature from about 120° C. to about 300° C., preferably from about 150° C. to about 250° C. and most preferably at about 200° C. Catalysts for the dehydroxylation process include weakly acidic metal oxides; such as the oxides of Al, Be, Zr and W; the weakly acid phosphates of Ca, Al, Mo, B and W; aluminosilicates in the H form, including zeolites; and ammonium salts, such as halides, sulfates and phosphates. Preferred catalysts are ZnO, MgO, $Sb_2O_3$ and BaO. The process may occur at any pressure such as atmospheric pressure. The pyrolytic dehydroxylation process may be accomplished in a single step as part of the distillation of electrolysis products remaining in the cell after termination of the anodic oxidation process, thereby eliminating the separate process step of recovering the oxylated compound.

The dehydroxylating process produces an unsaturated compound, preferably of the following formula, which is inertly substituted as are the precursor and oxylated compound described above:

$$\begin{array}{c} O \qquad\qquad R^5 \\ \| \qquad\qquad | \\ C-X-(CH_2)_n-C=CR^6 \\ \underline{\phantom{XXXXX}S\phantom{XXXXX}} \end{array}$$

in which X, $R^5$, $R^6$ and n are as previously defined. Preferred is the dehydroxylating process in which the precursor is monothioethylene carbonate.

Having described the invention, the following example is provided as further illustration of the invented process and not to limit the scope of the claims.

EXAMPLE 1

Two platinum electrodes are immersed into a solution of 5.2 g (0.050 mole) of ethylene monothiocarbonate, $$\begin{array}{c} O \\ \diagup \diagdown \\ | \quad\rangle=O \\ \diagdown \diagup \\ S \end{array}$$

0.15 g (0.018 mole) of sodium acetate and 20 ml of acetic acid in a 40-ml beaker. Electricity (0.10 Faradays) at a rate of 0.5 Amp is passed through the solution. The acetic acid is then removed under vacuum. The resulting residue, after aqueous sodium bicarbonate wash and ether extraction, is isolated by distillation at 120° C.–130° C. at 10 mm Hg pressure. The yield is 96 percent of 4-acetoxyethylene monothiocarbonate. A catalytic amount of sodium acetate and 2.0 g (0.012 mole) of 4-acetoxyethylene monothiocarbonate $$\begin{array}{c} O \qquad\qquad O \\ \| \qquad \diagup \diagdown \\ CH_3CO-\!\!-\!\!| \quad\rangle=O \\ \diagdown \diagup \\ S \end{array}$$

are contacted in a stirred 25-ml round-bottom flask at a temperature of 190° C. to 200° C. 2-Oxathiolone $$\begin{array}{c} O \\ \diagup \diagdown \\ | \quad\rangle=O \\ \diagdown \diagup \\ S \end{array}$$

is collected by distillation from the product reaction at 190° C. to 200° C. The yield of 2-oxathiolone is 50 percent based on ethylene monothiocarbonate.

I claim:

1. A process for forming oxylated derivatives of heterocyclic thiocarbonyl compounds comprising the step of contacting a heterocyclic precursor represented by the following formula $$\begin{array}{c} O \qquad\qquad R^5 \quad H \\ \| \qquad\qquad | \quad\; | \\ C-X-(CH_2)_n-\underset{|}{C}-\underset{|}{C}-R^6 \\ \phantom{C-X-(CH_2)_n-C}H \\ \underline{\phantom{XXXXXX}S\phantom{XXXXXX}} \end{array}$$

in which
X is selected from the group of bivalent moieties O, S, $CR^7R^8$ and $NR^9$;
$R^5$, $R^6$, $R^7$, $R^8$ and $R^9$ are independently selected from the group of monovalent moieties hydrogen, lower alkyl, aryl and acyl; and
n is between 0 and about 15;
with an oxylating agent which is represented by the formula $R^4OM_{1/y}$ in which $R^4$ is alkyl or acyl and M is either hydrogen or a metal cation of charge y under anodic alkoxylation or acyloxylation conditions sufficient to form an oxylated derivative represented by the formula:

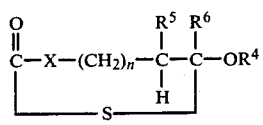

in which X, $R^4$, $R^5$, $R^6$ and n are as previously defined.

2. The process of claim 1 in which n is between 0 and about 3.

3. The process of claim 1 in which n is 0.

4. A process according to claim 1 in which the supporting electrolyte is present in an amount from about 1 percent to about 20 percent by weight of the total electrolysis solution.

5. A process according to claim 1 in which the molar ratio of cyclic precursor to $C_{1-4}$ alcohol or carboxylic acid is from about 1:2 to about 1:50.

6. A process according to claim 1 in which the temperature is from about 0° C. to about 70° C.

7. The process of claim 1 in which X is selected from the group of bivalent moieties O or $NR^9$ in which $R^9$ is as previously defined.

8. A process according to claim 1 in which the supporting electrolyte is selected from the group consisting of the alkali metal, alkaline earth metal, ammonium and quaternary ammonium salts of perchloric acids; tetrafluoroborohydrate, $BF_3$, $FeCl_3$, hexafluorophosphoric acid, hydrofluoric acid, nitric acid, hydrochloric acid, sulfuric acid, lower carboxylic acids, lower alkyl sulfonic acids, $C_{6-12}$ aryl sulfonic acids, and salts of the Bronsted acids listed.

9. A process according to claim 8 in which the supporting electrolyte is a quaternary ammonium salt of p-toluene sulfonic acid and acetic acid is not a solvent.

10. A process for producing a mono-unsaturated heterocyclic thiocarbonyl which comprises (1) contacting a heterocyclic precursor represented by the following formula

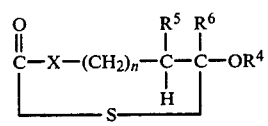

in which
X is selected from the group of bivalent moieties O, S, $CR^7R^8$ and $NR^9$;
$R^5$, $R^6$, $R^7$, $R^8$ and $R^9$ are independently selected from the group of monovalent moieties hydrogen, lower alkyl, aryl and acyl; and
n is between 0 and about 15;
with an oxylating agent which is represented by the formula $R^4OM_{1/y}$ in which $R^4$ is alkyl or acyl and M is either hydrogen or a metal cation of charge y under anodic alkoxylation or acyloxylation conditions sufficient to form an oxylated derivative represented by the formula:

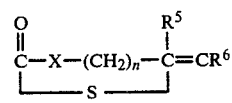

in which X, $R^4$, $R^5$, $R^6$ and n are as previously defined and (2) dehydroxylating by heating the oxylated derivative to produce a compound represented by the following formula:

$$\begin{array}{c} \text{O} \quad\quad\quad R^5 \\ \| \quad\quad\quad\quad | \\ \text{C—X—(CH}_2)_n\text{—C}=CR^6 \\ \underline{\quad\quad S \quad\quad} \end{array}$$

in which X is selected from the group of bivalent moieties O, S, $CR^7R^8$ and $NR^9$; $R^5$ and $R^6$ are independently selected from the group of monovalent moieties hydrogen, lower alkyl, aryl and acyl; and n is between 0 and about 15.

11. The process of claim 10 in which the dehydroxylation occurs at a temperature between about 120° C. and about 300° C.

12. The process of claim 11 in which the dehydroxylation occurs at about 200° C.

13. A process according to claim 12 in which the precursor is monothioethylene carbonate.

* * * * *